United States Patent [19]

Cisneros et al.

[11] Patent Number: 5,476,984
[45] Date of Patent: Dec. 19, 1995

[54] HYDRODECHLORINATION PROCESS AND CATALYST FOR USE THEREIN

[75] Inventors: Mark D. Cisneros; Michael T. Holbrook, both of Baton Rouge, La.; Larry N. Ito, Midland, Mich.

[73] Assignee: The Dow Chemical Company, Midland, Mich.

[21] Appl. No.: 397,315

[22] Filed: Mar. 2, 1995

Related U.S. Application Data

[63] Continuation of Ser. No. 227,841, Apr. 14, 1994, abandoned.

[51] Int. Cl.$^6$ .................................................. C07C 1/00
[52] U.S. Cl. .................................................. 585/733
[58] Field of Search ........................................ 585/733

[56] References Cited

U.S. PATENT DOCUMENTS 3,892,818  7/1975  Scharfe et al. .................... 260/676 R
4,895,995  1/1990  James et al. ....................... 585/310
4,899,001  2/1990  Kalnes et al. ..................... 585/310
4,943,671  7/1990  Dockner et al. ................... 585/642
5,105,032  4/1992  Holbrook et al. .................. 570/101

FOREIGN PATENT DOCUMENTS 5320076   12/1993  Japan .
WO9218447 10/1992  WIPO .

*Primary Examiner*—Asok Pal
*Assistant Examiner*—Nhat D. Phan

[57] ABSTRACT

A novel, improved process and catalyst are provided for the catalytic hydrodechlorination of a chlorinated alkane to its corresponding less-chlorinated and preferably non-chlorinated alkane, for example the hydrodechlorination of 1,2-dichloropropane to propane, the catalyst comprising a mixture of active Group VIII hydrogenating metals in elemental or compound form on a support.

4 Claims, No Drawings

HYDRODECHLORINATION PROCESS AND CATALYST FOR USE THEREIN

The present application is a continuation of application Ser. No. 08/227,841, filed on Apr. 14, 1994, now abandoned.

BACKGROUND OF THE INVENTION

The present invention relates to catalysts and processes for the catalytic hydrodechlorination of chlorinated alkanes such as 1,2-dichloropropane (hereafter, PDC) to produce a corresponding less-chlorinated and especially a non-chlorinated alkane, for example propane, and hydrogen chloride.

U.S. Pat. No. 3,892,818 to Scharfe is exemplary of the known art, and broadly relates to processes for converting byproduct and waste "hydrocarbon chlorides" (PDC being one named example of such) to more useful and valuable, or less troublesome, "chlorine-free hydrocarbons" (propane) via a rhodium-containing catalyst. Combinations of rhodium with other metals or metal compounds are contemplated, those being named including palladium, platinum, ruthenium, iridium, iron, cobalt, nickel, copper, gold, vanadium, chromium, molybdenum or tungsten, and the salts, hydroxides, oxides or carboxylates of the alkali and alkaline earth metals.

U.S. Pat. No. 4,895,995 to James, Jr. et al. and U.S. Pat. No. 4,899,001 to Kalnes et al. are closely related, and describe processes for the simultaneous hydroconversion of a first feedstock comprising unsaturated, halogenated organic compounds and a second feedstock comprising saturated, halogenated organic compounds using, for example, a palladium on alumina catalyst. An example is given in each wherein propane is the predominant chlorine-free hydrocarbon produced.

U.S. Pat. No. 4,943,671 to Docknet describes the conversion of 1-chloropropane to propane using active carbon and iron oxide as a cocatalyst.

SUMMARY OF THE INVENTION

The present invention provides a novel, improved process and catalyst for the catalytic hydrodechlorination of a chlorinated alkane to its corresponding less-chlorinated and preferably non-chlorinated alkane, and more particularly and preferably provides a process for the catalytic hydrodechlorination of PDC to propane, using a catalyst comprising a mixture of active Group VIII hydrogenating metals in elemental or compound form on a support (where the Group VIII metals are those denominated as such according to the Periodic Table of the Elements, Sargent-Welch Scientific Company, Skokie, Ill., Catalog No. S-18806 (1979), namely, iron, cobalt, nickel, ruthenium, rhodium, palladium, osmium, iridium and platinum).

DETAILED DESCRIPTION OF PREFERRED EMBODIMENTS

In a preferred embodiment, PDC (a coproduct of propylene oxide manufacture via a conventional chlorohydrin process) is converted to propane via a catalyst which consists essentially of a mixture of active Group VIII hydrogenating metals in elemental or compound form on a support, and more preferably is converted to propane via a catalyst which consists entirely of a mixture of active Group VIII hydrogenating metals in elemental or compound form on a support.

Preferably these Group VIII metals will comprise platinum and ruthenium, but more preferably will consist essentially of platinum and ruthenium and most preferably will consist entirely of platinum and ruthenium, so that a most preferred catalyst for converting PDC to propane will be a bimetallic catalyst of platinum and ruthenium (in elemental or compound form) on a selected support.

Preferably by these processes at least about 10 percent of the PDC feed is converted to materials such as propane, but more preferably at least about 20 percent of the PDC is converted, and most preferably at least about 30 percent of the PDC is converted to products including propane.

The support in each of these various catalysts can be any of the known conventional inert supports, but is preferably silica or carbon, with carbon being most preferred. The carbon is preferably a high surface area carbon, for example, a carbon having a specific surface area in an unimpregnated condition of about 200 $m^2/g$ or more, especially about 400 $m^2/g$ or more, and most especially about 600 $m^2/g$ or more.

An example of a commercially-available carbon which has been found suitable for use in the present invention is a coal-based carbon produced by Calgon Carbon Corporation under the designation "BPLF3", and may generally be characterized as having a specific surface area of 1100 $m^2/g$ to 1300 $m^2/g$, a pore volume of 0.7 to 0.85 $cm^3/g$, and an average pore radius of 12.3 to 14 angstroms. Based on an X-ray fluorescence analysis of this carbon, a typical bulk composition of the BPLF3 carbon has been determined to be as follows (by weight percent): silicon, 1.5 percent; aluminum, 1.4 percent; sulfur, 0.75 percent; iron, 0.48 percent; calcium, 0.17 percent; potassium, 0.086 percent; titanium, 0.059 percent; magnesium, 0.051 percent; chlorine, 0.028 percent; phosphorus, 0.026 percent; vanadium, 0.010 percent; nickel, 0.0036 percent; copper, 0.0035 percent; chromium, 0.0028 percent; and manganese, 0.0018 percent (the remainder being carbon). Examples of other, high surface area carbons include a coconut-based carbon produced by Calgon Carbon Corporation under the designation PCB (having a published specific surface area of from 1150 to 1250 $m^2/g$ and a pore volume of 0.72 $cm^3/g$), and a wood-based carbon produced by Calgon Carbon Corp. as WSIV Special carbon (having a published or reported specific surface area of 1400 $m^2/g$, and a pore volume of 1.25 $cm^3/g$).

Although the examples below are directed to the hydrodechlorination of PDC to propane in the gas phase only, it is anticipated that the hydrodechlorination processes of the present invention may be conducted in the gas phase or in the liquid phase (in a batchwise or continuous manner, as desired) albeit under correspondingly different conditions. In general, in a gas phase process for the hydrodechlorination of PDC to propane wherein at least 10 percent of the PDC is converted to such less-chlorinated materials, reaction pressures can typically range from atmospheric up to about 1000 psig, with temperatures of from about 25 deg. C. to about 400 deg. C., residence times of from about 0.1 seconds to about 7,200 seconds, and hydrogen/PDC feed ratios ranging on a molar basis from about 0.2 to 1 up to about 100 to 1.

More preferably, reaction pressures will range from about 0 psig to no more than about 500 psig, with temperatures of from about 180 deg. C. to about 300 deg. C., residence times of from about 1 second to about 30 seconds, and hydrogen/PDC molar feed ratios of from about 0.5 to 1 to not more than about 50 to 1.

Most preferably, reaction pressures in the gas phase processes will range from about 0 psig to not more than about 200 psig, with temperatures of from about 150 deg. C. to about 250 deg. C., residence times of from about 1 second to about 20 seconds, and hydrogen/PDC molar feed ratios of from about 1 to 1 to about 5 to 1.

Because of the highly exothermic nature of the contemplated processes, preferably a high heat capacity inert, such as methane, will be incorporated into the feed to moderate the rate of reaction and the generation of heat therefrom. Such addition may optionally and preferably be accompanied by a staged addition of the PDC or other chlorinated alkane feedstock.

The present invention is more particularly illustrated by the examples which follow:

EXAMPLES 1–5

Several bimetallic catalysts were prepared which employed platinum in combination with a second active Group VIII hydrogenating metal on a Calgon BPLF3 activated carbon support, for evaluation in dechlorinating PDC to propane in the gas phase. Each of these catalysts was prepared in the same atomic metal ratio of platinum to the second active Group VIII hydrogenating metal (namely, 0.18:1), by coimpregnation from an aqueous solution of the chloride salts of the metals involved on the Calgon BPLF3 activated carbon, air-drying for eighteen hours at ambient temperatures, then oven-drying for 2 hours at 120 degrees Celsius. Catalysts were then prepared in the same manner which employed only a single Group VIII metal.

A catalyst charge as thus prepared (0.6 grams in each of Examples 1–5 and in each of the single Group VIII metal catalysts prepared for comparison and contrast) was then generally placed in a tubular reactor (comprised of Monel™ nickel alloy (unless specifically noted below all of the components, tubing and fittings of the test reactor apparatus were also made of Monel™ nickel alloy (Huntington Alloys, Inco Alloys International, Inc.), having a diameter (O.D.) of ½ inch (1.27 cm), and being 12 inches (30.5 cm) in length and located within an aluminum block heated by a cartridge heater and regulated via a computer to maintain a selected reaction temperature of 220 degrees Celsius) over a glass wool support contained in the center of the reactor tubing.

The catalyst was then covered with a plug of glass wool and dried for from 1 to 24 hours at 120 degrees Celsius under a nitrogen purge. The catalyst was then reduced by passing hydrogen through the reactor at a flow rate of 90 mL/minute for from 1 to 24 hours. The reaction temperature of 220 degrees Celsius was achieved, and the reaction temperature and hydrogen gas flow were allowed to equilibrate for about 1 hour before liquid PDC feedstock flow was started into the apparatus.

In each instance, liquid PDC was pumped via a high pressure syringe pump through 1.6 mm (O.D.) (1/16 inch) Monel™ nickel alloy tubing into a packed sample cylinder serving as a feed evaporator.

The 1/16th inch tubing extended almost to the center of the packed cylinder, which was heated to a vaporizing temperature of 180 degrees Celsius using electrical heat tracing. Vaporization of the PDC feedstock was accomplished in the feed line, so that the PDC was superheated when combined with the hydrogen feed stream. Thermocouples were used to monitor the skin temperature of the feed evaporator and the temperature of the gas exiting the feed evaporator, and the temperature of the feed evaporator was controlled by computer.

The hydrogen feed stream was metered (at a 3 to 1 molar ratio of hydrogen to PDC) to a preheater using a Model 8249 linear mass flow controller from Matheson Gas Products, Inc. Secaucus, N.J., with the preheater consisting of a packed sample cylinder wrapped with electrical heat tracing. Thermocouples were used to monitor both the skin temperature of the preheater and the temperature of the gas exiting the preheater. The preheater temperature was set and maintained at 140 degrees Celsius.

Vaporized PDC exiting the evaporator was mixed with the hydrogen gas from the preheater in a 2 foot (0.61 meter) long section of ¼ inch (0.64 cm) tubing maintained at a temperature of 140 degrees Celsius. The mixed gases then were passed into and reacted within the tubular reactor at the aforementioned reaction temperature of 220 degrees Celsius, under atmospheric pressure, with a 3:1 molar feed ratio of hydrogen to PDC and a 1 second residence time.

After reacting the PDC and hydrogen in the vapor phase in the tubular reactor thus prepared, the products from the reaction were passed to a gas sampling valve, which provided gaseous aliquots for online gas chromatographic analysis in a Hewlett-Packard Model 5890 Series II gas chromatograph (Hewlett-Packard Company). The gas chromatograph was equipped with a flame ionization detector, and used 30 meter by 0.53 millimeter (I.D.) 100 percent methyl silicone/fused silica and 30 meter by 0.53 millimeter (I.D.) porous polymer-lined fused silica columns to separate the various reaction products. Response factors were conventionally determined by injections of gravimetrically-prepared standards of the individual reaction products. These response factors were applied in conjunction with individual peak areas and the total mols of all reaction products to determine the mol percents of individual components in the reactor effluent, and the selectivity to individual reaction products.

The results from Examples 1–5 (and from the runs with the single metal catalysts) are reported in Table 1 below, and show that the Group VIII hydrogenating metal catalysts exhibit an effective synergism in a combination of the Group VIII metals for the contemplated dechlorination of PDC, having much increased activity compared to the activity that one might expect given the results with individual Group VIII metal catalysts:

TABLE 1

| Catalyst (Wt. %/Wt. %) | PDC Conversion (%) | Propane Selectivity (%) | Propylene Selectivity (%) | Other[a] (%) |
|---|---|---|---|---|
| 0.5 Pt | 29 | 99 | 0 | 1 |
| 0.26 Ru | 8 | 12 | 88 | 0 |
| 0.14 Fe | 2 | 1 | 66 | 33 |
| 0.5 Pt/0.8 Fe | 85 | 99 | 1 | 0 |
| 0.5 Pt/0.8 Co | 30 | 96 | 3 | 1 |
| 0.5 Pt/0.9 Ni | 38 | 60 | 38 | 2 |
| 0.5 Pt/2.7 Ir | 63 | 98 | 0 | 2 |
| 0.5 Pt/1.4 Ru | 93 | 98 | 0 | 2 |

[a]Largely 2-chloropropane;

Those skilled in the art will of course recognize that in practice, a significant amount of further experimentation with various weights and combinations of the Group VIII metals and with various reaction conditions will be appropriate in optimizing the conversion of PDC to propane, for example. Such routine experimentation is however, in the nature of optimization and well within the abilities of those skilled in the art given the examples and general guidance provided herein.

What is claimed is:

1. A process for the hydrodechlorination of a chlorinated alkane containing two or more carbons to reaction products including its corresponding, less-chlorinated alkane and hydrogen chloride, comprising reacting the chlorinated alkane with hydrogen in the presence of a bimetallic catalyst of a) platinum and b) ruthenium, iridium or iron in elemental or compound form on a support, under conditions effective to carry out such hydrodechlorination.

2. A process as defined in claim 1, wherein the catalyst is a bimetallic catalyst of platinum and ruthenium in elemental or compound form on a support.

3. A process as defined in claim 1, wherein the chlorinated alkane is 1,2-dichloropropane, and wherein propane is produced in predominance to other products besides hydrogen chloride.

4. A process as defined in claim 3, wherein the catalyst is a bimetallic catalyst of platinum and ruthenium in elemental or compound form on a support.

* * * * *